US011273029B2

(12) United States Patent
Emken et al.

(10) Patent No.: US 11,273,029 B2
(45) Date of Patent: Mar. 15, 2022

(54) INTRAOCULAR ACTIVE ACCOMMODATION SYSTEM

(71) Applicant: Verily Life Sciences LLC, South San Francisco, CA (US)

(72) Inventors: Jeremy L. Emken, Belmont, CA (US); Shungneng Lee, Sunnyvale, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 238 days.

(21) Appl. No.: 16/333,499

(22) PCT Filed: Sep. 26, 2017

(86) PCT No.: PCT/US2017/053501
§ 371 (c)(1),
(2) Date: Mar. 14, 2019

(87) PCT Pub. No.: WO2018/064061
PCT Pub. Date: Apr. 5, 2018

(65) Prior Publication Data
US 2019/0254811 A1  Aug. 22, 2019

Related U.S. Application Data

(60) Provisional application No. 62/400,214, filed on Sep. 27, 2016.

(51) Int. Cl.
*A61F 2/16* (2006.01)

(52) U.S. Cl.
CPC .......... *A61F 2/1627* (2013.01); *A61F 2/1624* (2013.01); *A61F 2002/1682* (2015.04);
(Continued)

(58) Field of Classification Search
CPC ........................................ A61F 2/1624–2/1635
(Continued)

(56) References Cited

U.S. PATENT DOCUMENTS 5,843,188 A * 12/1998 McDonald ............ A61F 2/1629
128/898
7,261,736 B1  8/2007 Azar
(Continued)

FOREIGN PATENT DOCUMENTS

WO  2010/104654 A1  9/2010

OTHER PUBLICATIONS

International Search Report and Written Opinion from the International Searching Authority dated Dec. 8, 2017, for International Application No. PCT/US2017/053501, filed Sep. 26, 2017, 14 pages.
(Continued)

*Primary Examiner* — David H Willse
(74) *Attorney, Agent, or Firm* — Christensen O'Connor Johnson Kindness PLLC

(57) ABSTRACT

An intraocular lens (IOL) includes one or more haptic structures coupled to hold the IOL (100A) system in an eye. The IOL also includes one or more mechanical-to-electrical transducers (107) that detect mechanical changes in the eye and, in response to the mechanical changes, output an electrical signal. An accommodation actuator (101) is electrically coupled to the one or more mechanical-to-electrical transducers, and in response to the electrical signal the optical power of the accommodation actuator changes.

21 Claims, 8 Drawing Sheets

(52) U.S. Cl.
CPC .............. *A61F 2002/1683* (2013.01); *A61F 2002/16901* (2015.04); *A61F 2250/0001* (2013.01); *A61F 2250/0091* (2013.01); *A61F 2250/0096* (2013.01)

(58) Field of Classification Search
USPC .............................................. 623/6.22, 6.37
See application file for complete search history.

(56) References Cited

U.S. PATENT DOCUMENTS

| | | |
|---|---|---|
| 8,454,688 B2 | 6/2013 | Esch et al. |
| 9,226,818 B2 | 1/2016 | Campin et al. |
| 2006/0095128 A1* | 5/2006 | Blum .................... A61F 2/1627 623/6.37 |
| 2007/0088433 A1 | 4/2007 | Esch et al. |
| 2015/0173891 A1 | 6/2015 | Devita Gerardi et al. |
| 2016/0030162 A1* | 2/2016 | Simonov ............... A61F 2/1629 623/6.22 |
| 2016/0081793 A1 | 3/2016 | Galstian et al. |

OTHER PUBLICATIONS

European Office Action dated Jan. 13, 2021, in corresponding European Patent Application No. 17780966.2, 5 pages.

\* cited by examiner

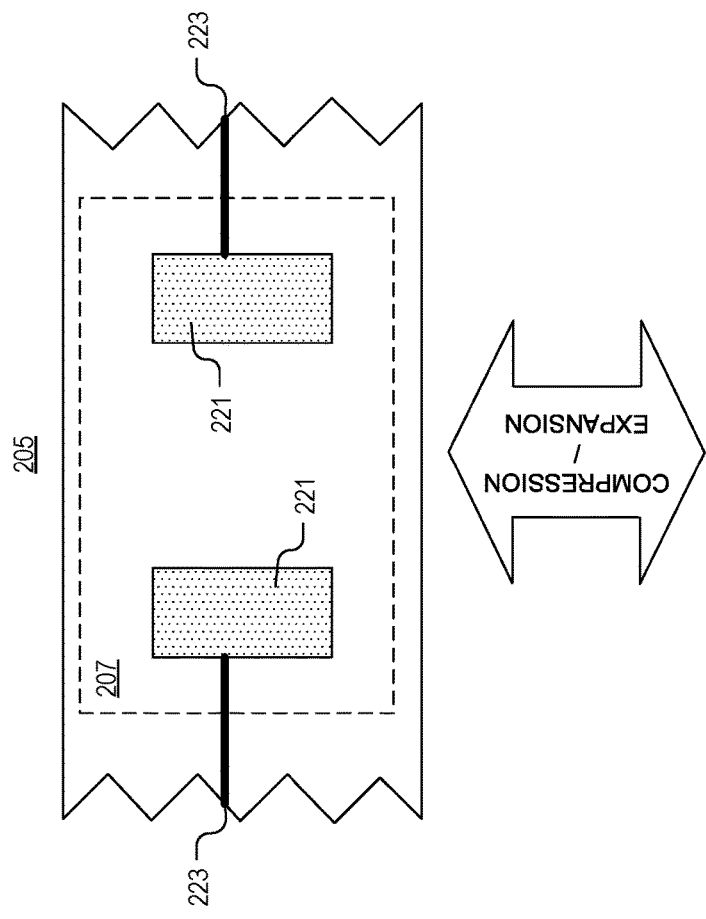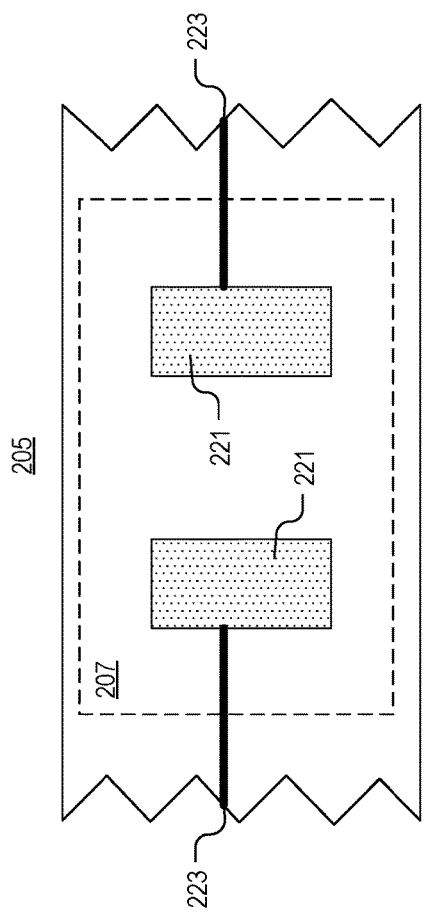
FIG. 2A
FIG. 2B

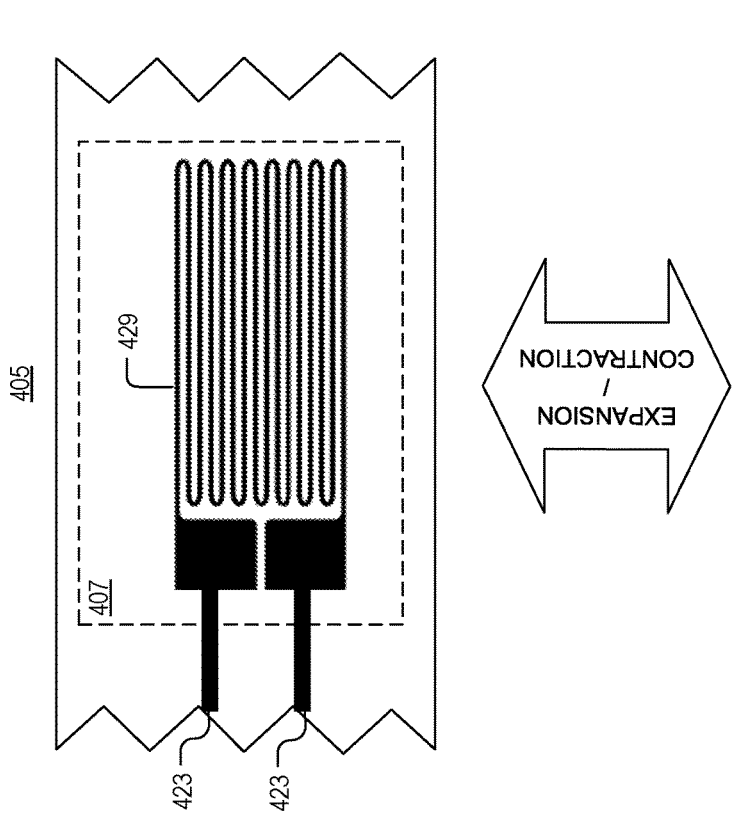
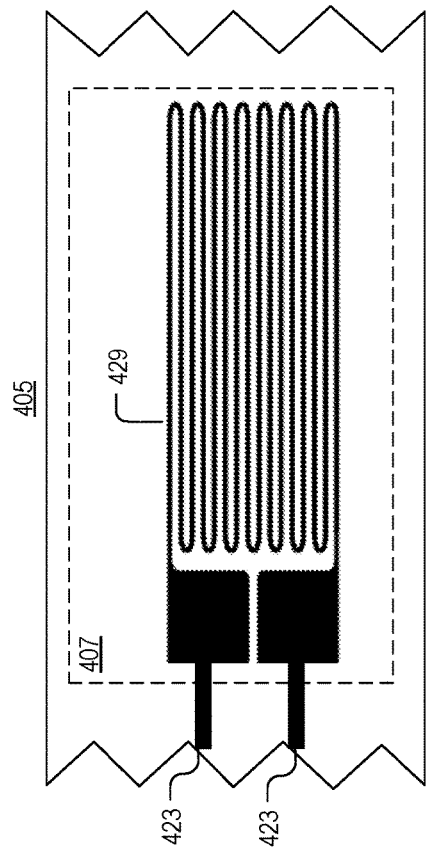
FIG. 4A
FIG. 4B

INTRAOCULAR ACTIVE ACCOMMODATION SYSTEM

CROSS-REFERENCE TO RELATED APPLICATIONS

This application claims the benefit of U.S. Provisional Application No. 62/400,214, filed Sep. 27, 2016, which is incorporated by reference in its entirety.

TECHNICAL FIELD

This disclosure relates generally to the field of optics, and in particular but not exclusively, relates to intraocular lenses (IOLs).

BACKGROUND INFORMATION

Accommodation is a process in which the eye adjusts its focal distance to maintain focus on objects of varying distance. Accommodation is a reflex action, but can be consciously manipulated. Accommodation is controlled by contractions of the ciliary muscle. The ciliary muscle encircles the eye's elastic lens and applies a force on the elastic lens during muscle contractions that change the focal point of the elastic lens.

As an individual ages, the effectiveness of the ciliary muscle degrades. Presbyopia is a progressive age-related loss of accommodative or focusing strength of the eye, which results in increased blur at near distances. This loss of accommodative strength with age has been well studied and is relatively consistent and predictable. Presbyopia affects nearly 1.7 billion people worldwide today (110 million in the United States alone) and that number is expected to substantially rise as the world's population ages. Techniques and devices that can help individuals offset the effects of Presbyopia are increasingly in demand. Intraocular lenses (IOLs) are used to treat a wide variety of physical maladies including near-sightedness, far-sightedness, astigmatism, and cataracts. IOLs are placed within an eye by cutting the eye open and inserting the IOL. Typically an IOL includes a small lens with side struts, called haptics, which are used to hold the lens in place inside the eye.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

FIGS. 2A and 2B illustrate a capacitive mechanical-to-electrical transducer, in accordance with an embodiment of the disclosure.

FIGS. 4A and 4B illustrate a resistive mechanical-to-electrical transducer, in accordance with an embodiment of the disclosure.

DETAILED DESCRIPTION

Embodiments of an apparatus and method for intraocular accommodation are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The instant disclosure provides a system and method for intraocular accommodation using mechanical-to-electrical transducers to measure movement of the eye during its natural accommodation process. Although the eyes using the lens disclosed here cannot naturally accommodate (since the natural lens has been removed and replaced with an artificial lens), the ciliary muscles still contract when the eye focuses at different depths. These contractions may be measured by mechanical-to-electrical transducers on the implanted intraocular device. The signal output from the mechanical-to-electrical transducers may be used to control the optical power of an accommodation actuator disposed within the lens. The lens may accommodate to the same optical power as the user's natural lens.

Figure 1A:
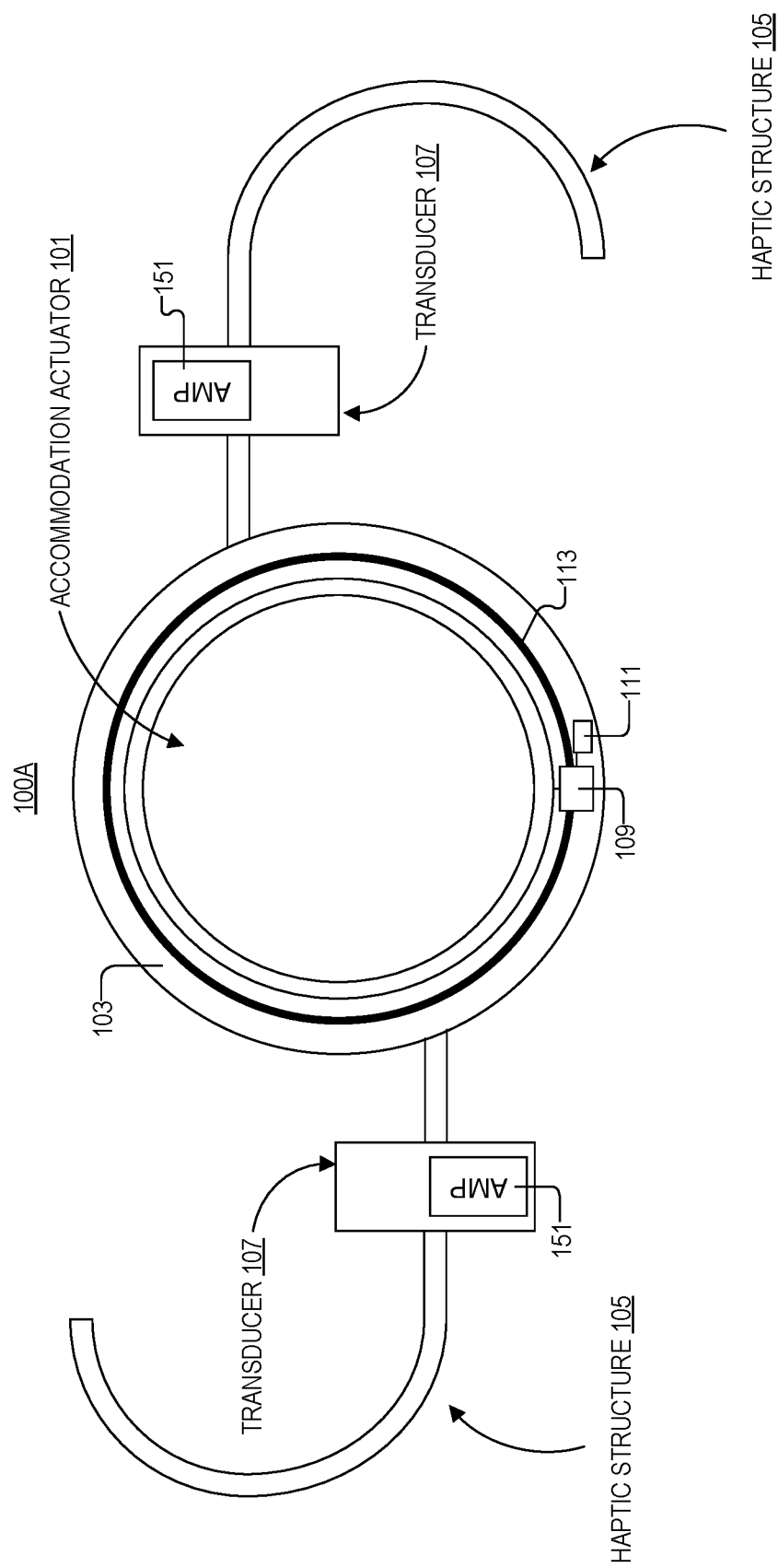
FIG. 1A illustrates an active accommodation intraocular lens (IOL), in accordance with an embodiment of the disclosure.

FIG. 1A illustrates an active accommodation intraocular lens (IOL) 100A, in accordance with an embodiment of the disclosure. IOL 100A includes accommodation actuator 101, transparent encapsulant 103, haptic structures 105, mechanical-to-electrical transducers 107, accommodation controller 109, power supply 111, charging circuitry 113, and amplification circuitry 151.

As illustrated, one or more haptic structures 105 are coupled to hold IOL 100A in an eye (with outward spring-like pressure), and coupled to accommodation actuator 101. One or more mechanical-to-electrical transducers 107 are coupled to one or more haptic structures 105, and detect mechanical changes in the eye of the IOL user. In response to these mechanical changes, one or more mechanical-to-electrical transducers 107 output an electrical signal to accommodation actuator 101. Accommodation actuator 101 is electrically coupled to one or more mechanical-to-electrical transducers 107, and in response to the electrical signal, accommodation actuator 101 changes its optical power. As will be discussed in greater detail later, this change in optical power may be determined by logic (software, hardware, or a combination of the two) in accommodation controller 109. In one embodiment, accommodation actuator 101 includes a liquid crystal element, and the optical power of the liquid crystal element changes in the presence of an electric field. For example, accommodation actuator 101 may be implemented using a layer of a liquid crystal material (e.g., nematic, twisted nematic, cholesteric, or blue phase liquid crystal) disposed within an enclosure material. Liquid crystalline materials are one example of an effective technology, and may be adapted to achieve a shift in refractive index greater than 0.2 in response to an applied voltage of less than 5.0 Volts. Such a shift in refractive index is capable of providing a level of accommodation to correct near vision in presbyopic patients. Alternatively, accommodation actuator 101 may include an electrowetting lens system (where the optical power changes as a function of liquid contact angle), or a micro-lens system (where the optical power changes via mechanical adjustment of the lenses). In other embodiments, accommodation actuator 101 may be implemented using other types of dynamic optical materials such as electro-optic materials that vary refractive index in the presence of an applied electric field. Accommodation actuator 101 may be a distinct device embedded within IOL 100A, or a bulk material having a controllable refractive index. In yet another embodiment, accommodation actuator 101 may be implemented using a deformable lens structure that changes shape under the influence of an electrical signal. However, one skilled in the art will appreciate that accommodation actuator 101 may include many electrical and mechanical systems that have the ability to change their optical power, in accordance with the teachings of the present disclosure.

In the depicted embodiment, accommodation actuator 101 may not receive the electrical signal directly from the one or more mechanical-to-electrical transducers 107, because accommodation controller 109 is electrically coupled between the one or more mechanical-to-electrical transducers 107 and accommodation actuator 101. In response to the electrical signal, accommodation controller 109 determines a magnitude of the change of the optical power in accommodation actuator 101. Additionally, amplification circuitry 151 is coupled to the one or more mechanical-to-electrical transducers 107 to receive the electrical signal and amplify the electrical signal. The amplified electrical signal is then sent to accommodation controller 109. Amplifying the signal output from one or more mechanical-to-electrical transducers 107 may help to more precisely control accommodation actuator 101 and eliminate error.

In the illustrated embodiment, amplification circuitry 151 and mechanical-to-electrical transducers 107 are disposed on the one or more haptic structures 105. This may allow for precise measurement of the stress/strain imparted on haptic structures 105 from the eye's natural accommodative process. One or more mechanical-to-electrical transducers 107 may measure stress, strain, shear stress/strain, or any other physical measurement to glean useful information about how much the eye is trying to accommodate. For example, the electrical signal from one or more mechanical-to-electrical transducers 107 may be proportional or commensurate to movement of a pseudophakic capsular bag, occurring during the eye's accommodative process (see e.g., FIG. 1C). In this case, predefined movement actions of the pseudophakic capsular bag may correspond to predefined optical power settings, and accommodation controller 109 can adjust accommodation actuator 101 accordingly. In one embodiment, one or more mechanical-to-electrical transducers 107 include at least one of a strain gauge, a pressure sensor, a piezoelectric sensor, piezoresistive sensor, or a capacitive sensor (see infra FIGS. 2A-5B). In the depicted embodiment, one or more mechanical-to-electrical transducers 107 are included in an enclosed box with amplification circuitry 151, and the box is disposed midway along the haptic structures 105. However, as will be shown in FIG. 1B, one or more mechanical-to-electrical transducers 107 may be disposed anywhere on IOL 100A, and optimized to detect mechanical movement of the eye. For instance, to improve sensitivity, mechanical-to-electrical transducers 107 may be placed at the area of highest strain/pressure/force which may be at the haptic-optic junction, in the middle of haptic, or at the end of the haptic. One skilled in the art will appreciate that the illustrated location of mechanical-to-electrical transducers 107 is merely an example of transducer location, and that showing every possible transducer configuration is not amenable to illustration.

Also shown in FIG. 1A is power supply 111 electrically coupled to one or more mechanical-to-electrical transducers 107 and accommodation actuator 101. Power supply 111 generally provides power to the whole of IOL 100A. Further, power supply 111 is coupled to charging circuitry 113 to charge power supply 111. In the depicted embodiment, charging circuitry 113 includes an inductive charging ring which may be charged by placing the ring in an oscillating electromagnetic field. The inductive charging ring may also have another purpose: communicating with other electronic devices outside of the eye via backscatter methods. For example, while the user is sleeping, an electronic facemask may be worn, the facemask my send an alternating RF signal to IOL 100A. This may both charge power supply 111 and allow communication with outside electronics via the facemask. The facemask may be plugged in to a computer via USB port or the like to analyze data about the users vision and possibly make adjustments to IOL 100A. In other embodiments, charging circuitry 113 may also include a photovoltaic device which provides power by passively absorbing light entering the user's eye.

In some embodiments, all of the circuitry described above may be mounted on a substrate. The substrate may include one or more surfaces suitable for mounting accommodation controller 109, power supply 111, and inductive charging ring (charging circuitry 113). The substrate can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or silver nanowire mesh) can be patterned on the substrate to form circuitry, electrodes, etc. For example, inductive charging ring can be formed by depositing a pattern of gold or another conductive material on the substrate. Similarly, interconnects can be formed by depositing suitable patterns of conductive materials on the substrate. A combination of resists, masks, and deposition techniques can be employed to pattern materials on the substrate. The substrate can be a relatively rigid material, such as polyethylene terephthalate ("PET"), silicon, or another material sufficient to structurally support the circuitry and/or electronics within encapsulant 103. In some embodiments, the substrate is flexible or segmented to permit folding of IOL 100A and facilitate insertion into the eye. In one embodiment, encapsulant 103 includes a bio-compatible polymer like PMMA or PDMS. IOL 100A can alternatively be arranged with a group of unconnected substrates rather than a single substrate. For example, accommodation controller 109 and power supply 111 can be mounted to one substrate, while the inductive charging ring is mounted to another substrate and the two can be electrically connected via interconnects. The substrate may also be a continuous piece of semiconductor, housing all or some of the aforementioned pieces of device architecture as integrated circuitry.

The substrate can be shaped as a flattened ring with a radial width dimension sufficient to provide a mounting platform for the embedded electronic components. The substrate can have a thickness sufficiently small to allow the substrate to be embedded in encapsulant 103 without adversely influencing the profile of IOL 100A. For example, the substrate can be shaped as a ring with a diameter of about 10 millimeters, a radial width of about 1 millimeter (e.g., an outer radius 1 millimeter larger than an inner radius), and a thickness of about 50 micrometers.

Accommodation controller 109 contains logic to choreograph the operation of the other embedded components (not only control accommodation actuator 101). Logic in accommodation controller 109 controls the general operation of IOL 100A, including providing a logical user interface, power control functionality, etc. This accommodation logic includes logic for receiving signals from sensors monitoring the orientation of the device, determining the current gaze direction or focal distance of the user, and manipulating accommodation actuator 101 (focal distance of the lens) in response to these physical cues. The auto-accommodation can be implemented in real-time based upon feedback from the one or more mechanical-to-electrical transducers 107, or permit the user to select specific accommodation regimes (e.g., near-field accommodation for reading, far-field accommodation for regular activities, etc.). Accommodation controller 109 may have communication logic that provides communication protocols for wireless communication with a reader via inductive charging ring (which can also be used as an RF antenna). In one embodiment, the communication logic provides backscatter communication via the inductive charging ring when in the presence of an electromagnetic field output from a reader. In one embodiment, the communication logic operates as a smart wireless radio-frequency identification ("RFID") tag that modulates the impedance of inductive charging ring for backscatter wireless communications. The various logic modules of accommodation controller 109 may be implemented in software/firmware executed on a general purpose microprocessor, in hardware (e.g., application specific integrated circuit), or a combination of both.

Eye-mountable device 100 may include other embedded electronics and logic modules. For example, a light source or pixel array may be included to provide visible feedback to the user. An accelerometer or gyroscope may be included to provide positional, rotational, directional or acceleration feedback information to accommodation controller 109.

Figure 1B:
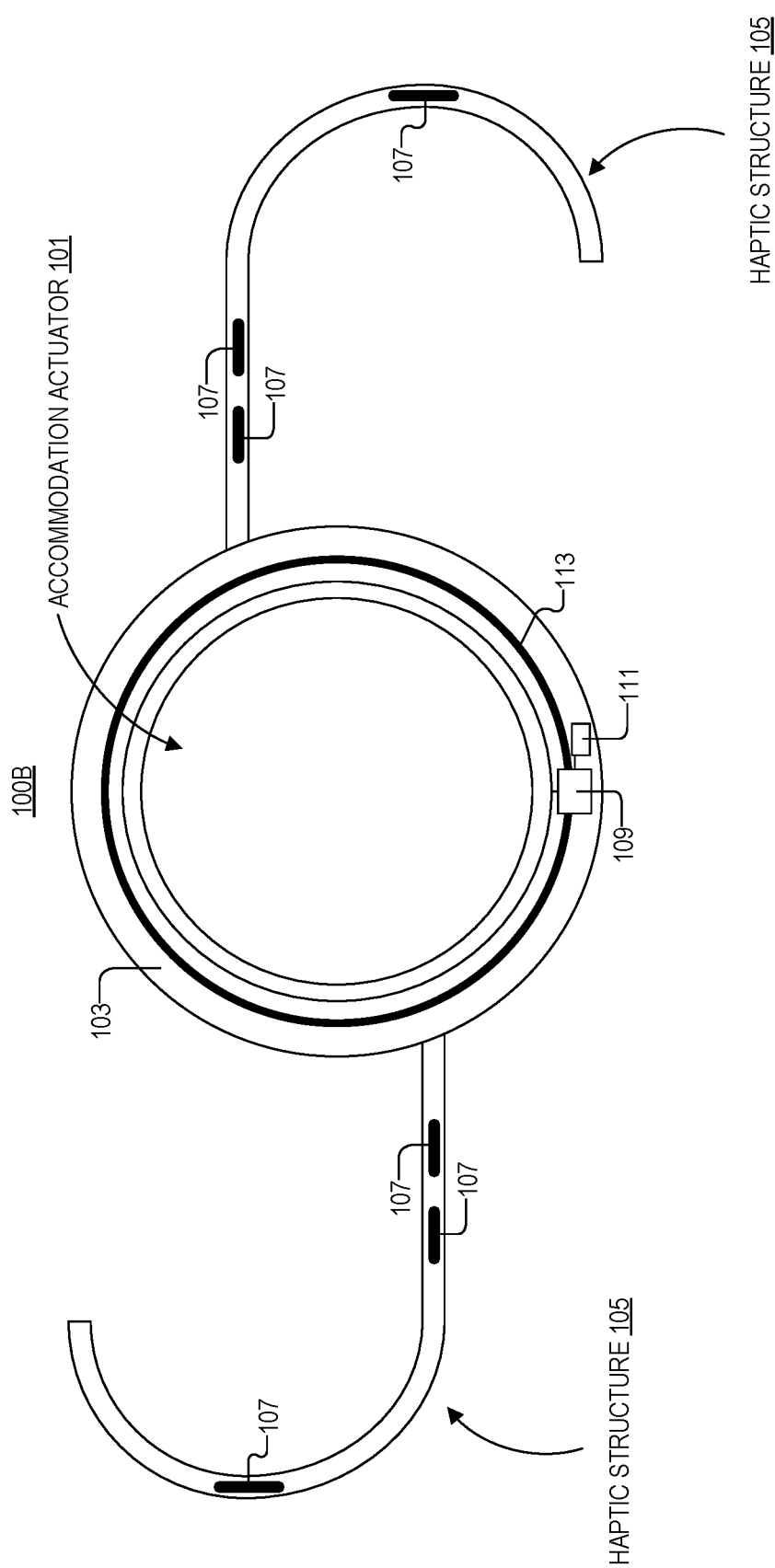
FIG. 1B illustrates an active accommodation IOL, in accordance with an embodiment of the disclosure.

FIG. 1B illustrates an active accommodation IOL 100B, in accordance with an embodiment of the disclosure. IOL 100B is similar in many ways to IOL 100A; however, one major difference is that one or more mechanical-to-electrical transducers 107 are highly miniaturized and deposed in multiple locations along haptic structures 105. For example, two of mechanical-to-electrical transducers 107 are disposed on each linear portion of haptic structures 105 while another mechanical-to-electrical transducer 107 is disposed at the midpoint of the arced portion of haptic structures 105. This configuration may be used to detect the different components of stress/strain in IOL 100A. For example the two mechanical-to-electrical transducers 107 disposed on the linear portion of the haptic structure may be used to determine an X-component of stress or strain, while the mechanical-to-electrical transducers 107 disposed on the curved portion of the haptic structures 105 may be used to determine a Y-component of stress or strain. However, one skilled in the art will appreciate that mechanical-to-electrical transducers 107 do not have to be located on haptic structures 105 and may cover a large area of IOL 100B to effectively use the entire movement/compression of the device (not just the high strain areas). In some embodiments, stress/strain measurements may be used in conjunction with other types of measurement (e.g., electromyogram of ciliary muscles) to control IOL 100B. Furthermore, any of these sensors may be used to examine the shear stress/strain on the device. Additionally, the one or more mechanical-to-electrical transducers 107 may include redundant transducers to ensure the accuracy of the measurement or calculate the average stress/strain on the device. This may make the accommodative process less volatile and/or smooth transitions between accommodative states. In the measurement of deflection of IOL 100B, any of the following mechanical-to-electrical transducers 107 may be used: strain gages, goniometers, pressure transducers, ultrasound transducers, magnetometers, etc. Mechanical lever arms and/or relative positions could also serve to amplify the deflection signal or help configure other electrical designs to meet the measurement window of interest.

In the illustrated embodiment, amplification circuitry 151 and/or software is included in accommodation controller 109. Thus, when one or more mechanical-to-electrical transducers 107 measure some intraocular strain, the signal is transmitted directly to a portion of accommodation controller 109 to amplify the signal. One skilled in the art will appreciate that there are many ways to amplify a signal depending on the type of signal (e.g., voltage, current, AC current, DC current, etc.). Accordingly, in some embodiments a single transistor may suffice to amplify a voltage change experienced by the one or more mechanical-to-electrical transducers 107. However, in other embodiments more complex systems may be needed depending on the type of currently flowing through IOL 100B (e.g., AC or DC) and the type of transducer employed.

Figure 1C:
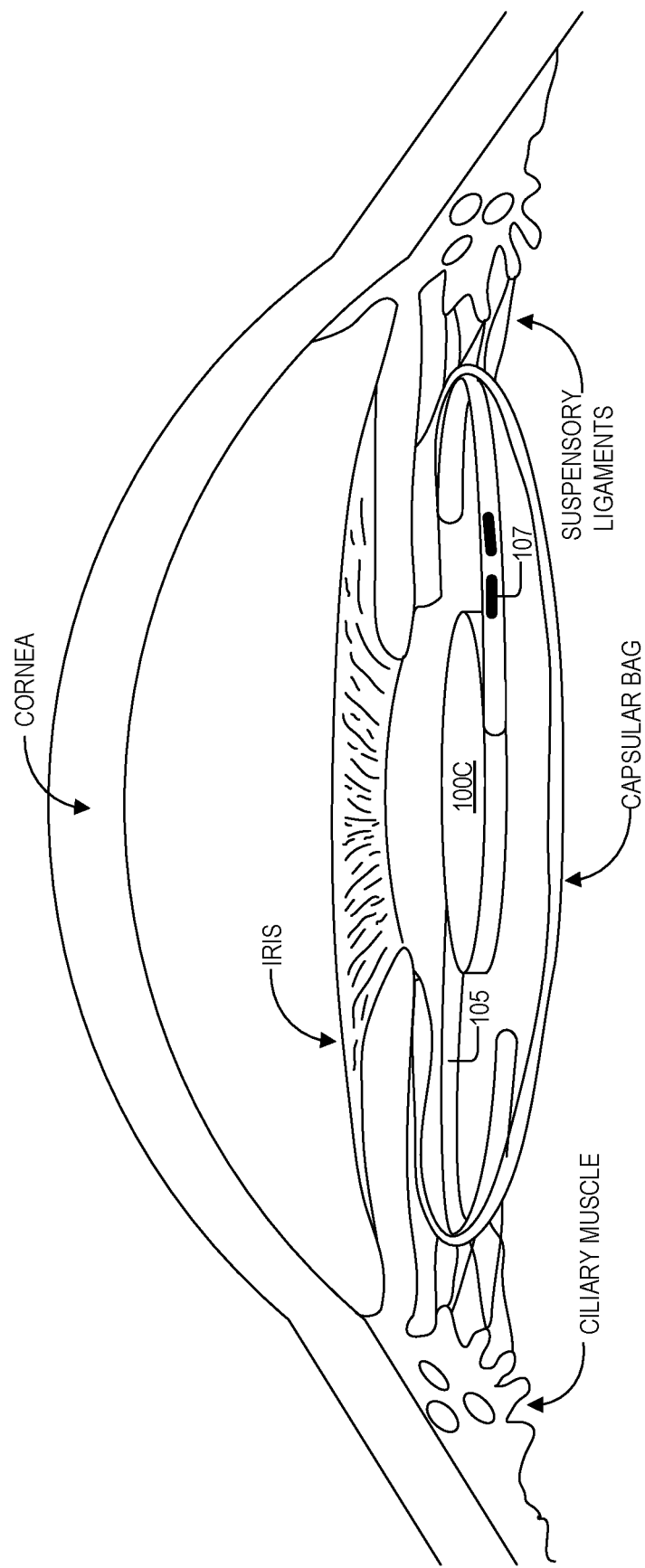
FIG. 1C illustrates an active accommodation IOL disposed in an eye, in accordance with an embodiment of the disclosure.

FIG. 1C illustrates an active accommodation IOL 100C disposed in an eye, in accordance with an embodiment of the disclosure. In the depicted embodiment, IOL 100C is the same or similar as IOL 100B from FIG. 1B. As illustrated, IOL 100C includes the highly miniaturized mechanical-to-electrical transducers 107 disposed on haptic structures 105. Since the haptic structures 105 center IOL 100C in the eye's capsular bag (pressing against the lateral edges of the capsular bag like an outward spring), mechanical-to-electrical transducers 107 can detect micron-scale movement/deflections (e.g., ~100 μm) of the capsular bag. The capsular bag may move when the ciliary muscles pull on suspensory ligaments attached to the capsular bag. This applied strain would control the optical power of the user's natural lens (if the user still had their natural lens). Mechanical-to-electrical transducers 107 may receive the strain signal, and may be placed on locations of IOL 100C that experience the largest amount of movement so that the strain signal they receive is very strong. Moreover, sensors may be contained entirely within IOL 100C to prevent degradation. As stated, the signal output from mechanical-to-electrical transducers 107 may be amplified. This signal may then be sent to the micro controller in IOL 100C to control the degree of accommodation of the accommodation actuator. The amount of accommodation may correspond to the force applied by the ciliary muscles so that IOL 100C accommodates in a similar manner as the user's natural lens would.

FIGS. 2A and 2B illustrate a capacitive mechanical-to-electrical transducer 207, in accordance with an embodiment of the disclosure. In one embodiment, capacitive mechanical-to-electrical transducer 207 may be included in IOL devices 100A and/or 100B. In FIG. 2A, the capacitive plates 221 are at their natural separation (no stress/strain on haptic structure 205); in FIG. 2B, the capacitive plates 221 are compressed (stress/strain induced in haptic structure 205).

In the illustrated embodiment, two capacitive plates 221 are disposed on the surface of a portion of haptic structure 205. The two capacitive plates 221 communicate to the other pieces circuitry via interconnects 223. As capacitive plates 221 move closer together and further apart, the capacitance between them changes. In a plate capacitor, capacitance is proportional to the surface area of the plates and inversely proportional to the separation between the plates. Accordingly, the capacitance between plates 221 is correlated to their separation distance. The separation of the plates can be correlated to the stress/strain on the haptic structure 205. These stress/strain measurements may be used to adjust the optical power of the accommodation actuator.

Capacitive plates 221 may include metals such as gold, silver, aluminum or the like, and may be deposited on the surface of the haptic structures 205. Alternatively, the grooves may be etched into haptic structures 205 and plates 221 are deposited in the grooves.

Figure 3A:
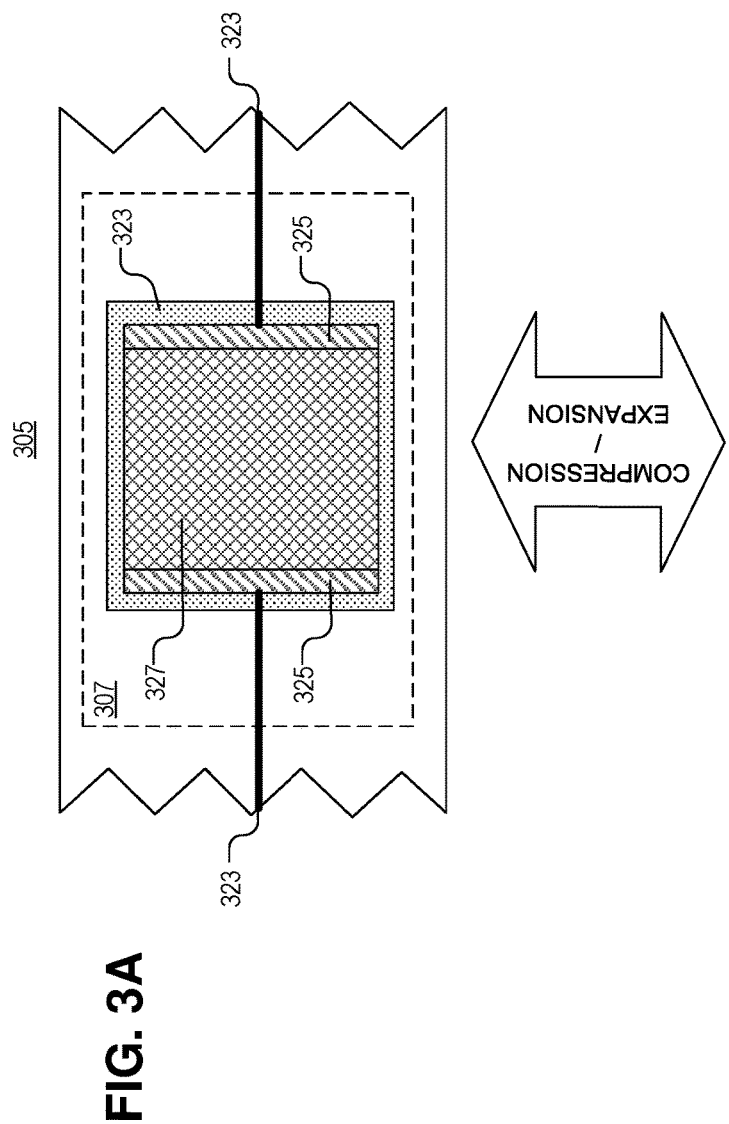
FIGS. 3A and 3B illustrate a piezoelectric mechanical-to-electrical transducer, in accordance with an embodiment of the disclosure.
Figure 3B:
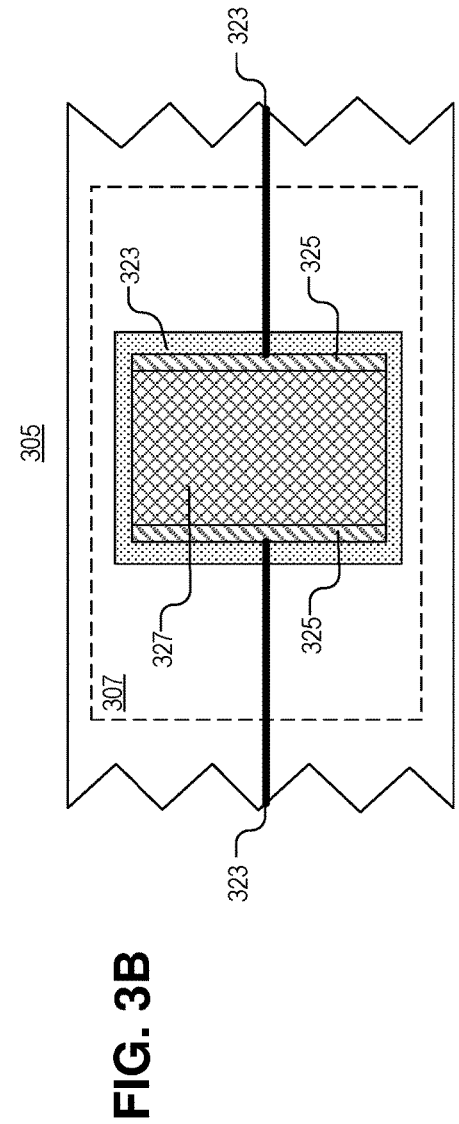

FIGS. 3A and 3B illustrate a piezoelectric mechanical-to-electrical transducer 307, in accordance with an embodiment of the disclosure. In one embodiment, piezoelectric mechanical-to-electrical transducer 307 may be included in IOL devices 100A and/or 100B. In FIG. 3A, piezoelectric mechanical-to-electrical transducer 307 is not compressed or stretched (no stress/strain on haptic structure 305); in FIG. 3B, the piezoelectric mechanical-to-electrical transducer 307 is compressed (stress/strain induced in haptic structure 305).

Piezoelectric mechanical-to-electrical transducer 307 includes two electrodes 325 disposed on opposite sides of piezoelectric material 327. Electrodes 325 and piezoelectric material 327 are disposed in an encapsulation material 323. The voltage across piezoelectric material 327 is sent back to other circuitry in the IOL device via interconnects 323 which may include a conductive material like copper, silver, or titanium.

In piezoelectric materials, charge accumulates in response to applied mechanical stress. The physical mechanism is understood as electromechanical interaction of atoms in a crystalline material with no inversion symmetry. The voltage is proportional to the stress applied to the crystal. In the depicted embodiment, piezoelectric mechanical-to-electrical transducer 307 may include materials like quartz, AlPO4, lithium niobate, or the like. One skilled in the art will understand that any piezoelectric material with sufficient sensitivity for the instant application may be employed, in accordance with the teachings of the present invention.

FIGS. 4A and 4B illustrate a resistive mechanical-to-electrical transducer 407, in accordance with an embodiment of the disclosure. In one embodiment, resistive mechanical-to-electrical transducer 407 may be included in IOL devices 100A and/or 100B. In FIG. 4A, resistive mechanical-to-electrical transducer 407 is not compressed or stretched (no stress/strain on haptic structure 405); in FIG. 4B, the resistive mechanical-to-electrical transducer 407 is compressed (stress/strain induced in haptic structure 405).

As shown, resistive mechanical-to-electrical transducer 407 includes a wire 429, S-curving many times between two electrodes. In metals, the resistivity increases with strain due to atomic lattice expansion and formation of defects. Accordingly, as the strain gage presented here expands and contracts, the resistivity will change. The voltage drop across the strain-gauge can be sent to the accommodation controller to control the optical power of the accommodation actuator. The signal may be sent by interconnects 423.

Figure 5A:
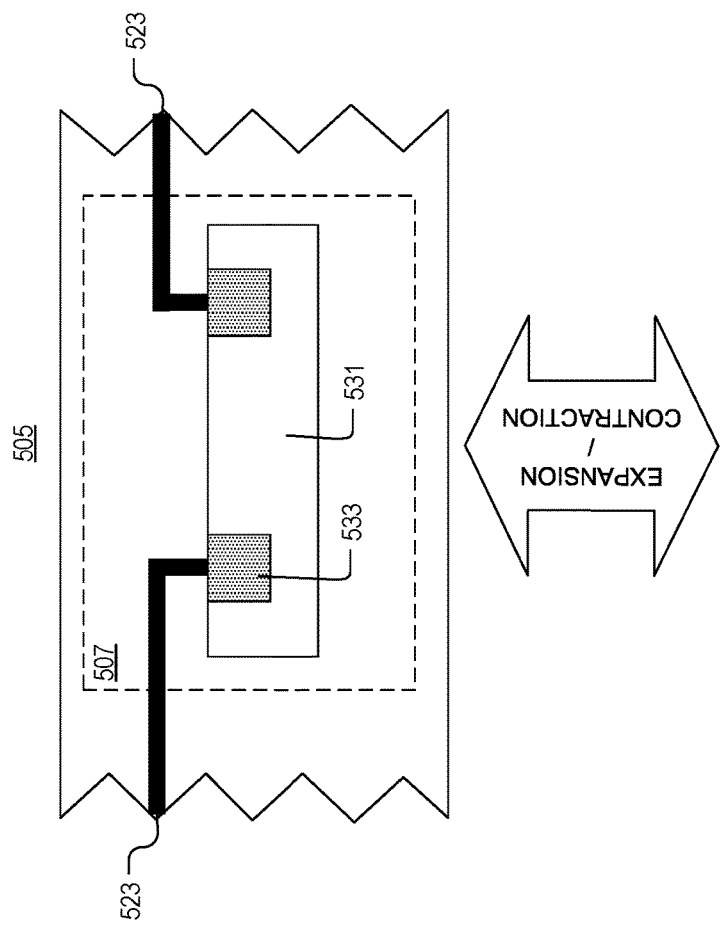
FIGS. 5A and 5B illustrate a piezoresistive mechanical-to-electrical transducer, in accordance with an embodiment of the disclosure.
Figure 5B:
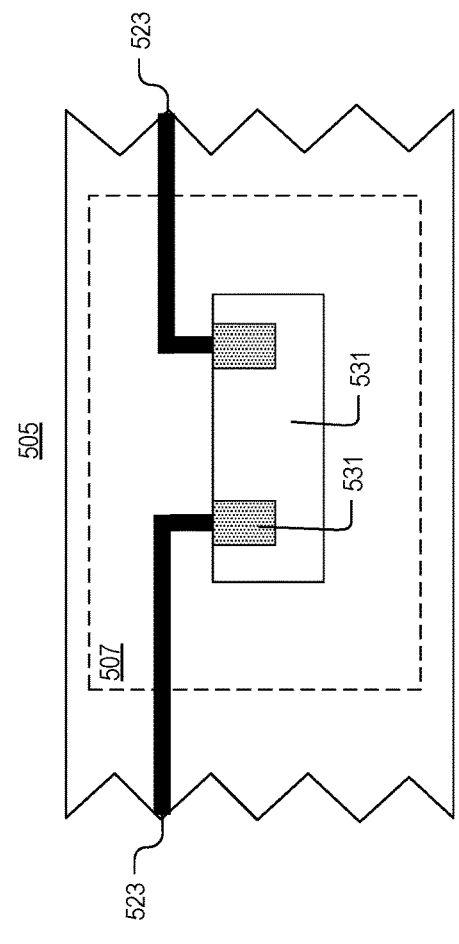

FIGS. 5A and 5B illustrate a piezoresistive mechanical-to-electrical transducer 507, in accordance with an embodiment of the disclosure. In one embodiment, piezoresistive mechanical-to-electrical transducer 507 may be included in IOL devices 100A and/or 100B. In FIG. 5A, piezoresistive mechanical-to-electrical transducer 507 is not compressed or stretched (no stress/strain on haptic structure 505); in FIG. 5B, the piezoresistive mechanical-to-electrical transducer 507 is compressed (stress/strain induced in haptic structure 505).

The piezoresistive mechanical-to-electrical transducer 507 includes a semiconductor material 531 and two highly doped semiconductor regions 533. When semiconductor material 531 expands or contracts, the conductivity of semiconductor material 531 changes. This change in conductivity may be correlated with the amount of expansion/contraction. Accordingly, the voltage across piezoresistive mechanical-to-electrical transducer 507 can be sent back to the accommodation controller via interconnects 523 to control the optical power of the accommodation actuator.

Figure 6:
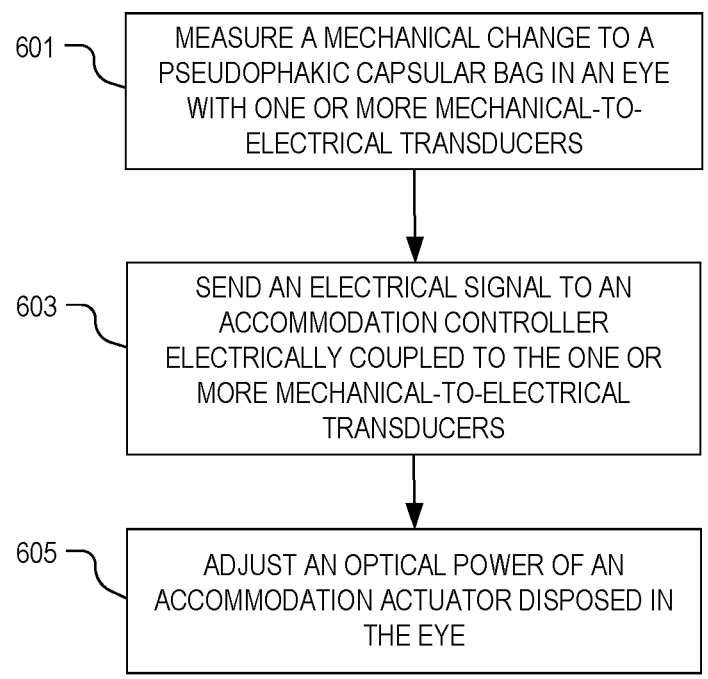
FIG. 6 illustrates a method of active accommodation, in accordance with an embodiment of the disclosure.

FIG. 6 illustrates a method of active accommodation, in accordance with an embodiment of the disclosure. The order in which some or all of the method blocks appear should not be deemed limiting. Rather, one of ordinary skill in the art having the benefit of the present disclosure will understand that some of the method blocks may be executed in a variety of orders not illustrated, or even in parallel. Additionally, blocks may be added to, or excluded from, method 600, in accordance with embodiments of the disclosure.

Block 601 illustrates measuring a mechanical change to a pseudophakic capsular bag in an eye with one or more mechanical-to-electrical transducers. As stated above, the transducers may be any kind of transducer with sufficient sensitivity for the instant application. A single type of transducer may be used in one device, or several different kinds may be used in the same device to elicit different types of stress/strain information.

Block 603 shows, in response to the mechanical change, sending an electrical signal to an accommodation controller electrically coupled to the one or more mechanical-to-electrical transducers. The accommodation controller will then interpret this electrical signal to determine how much to adjust the accommodation actuator. In some embodiments, the analog signal from the one or more mechanical-to-electrical transducers can be converted into a binary signal. Thus, if the measured stress/strain is above a certain level this will correspond to a particular power of optical accommodation. In other words, predefined movement actions of the pseudophakic capsular bag may correspond to predefined optical power settings. Alternatively, the electrical signal may remain analog, and the accommodation controller will adjust the optical power of the accommodation actuator proportional to the electrical signal received from the mechanical-to-electrical transducers. In some embodiments, both predetermined and proportional optical power adjustments are used.

In one embodiment, the electrical signal is amplified prior to sending the electrical signal to the accommodation controller. However, in other embodiments the controller itself may amplify the signal. Amplification circuitry may be disposed anywhere on the IOL device depending on the specific design/use case of the the IOL.

Block 605 discloses adjusting an optical power of an accommodation actuator disposed in an eye. The accommodation actuator is electrically coupled to the accommodation controller. Although in the depicted examples the one or more mechanical-to-electrical transducers, the accommodation controller, and the accommodation actuator are included in a single device, in other embodiments they may be distributed throughout the eye and tethered together via wires or may communicate wirelessly. However, in many embodiments, movement of the pseudophakic capsular bag is measured via mechanical deformation of the haptic structures.

Although only three primary process blocks are depicted in method 600, in other embodiments, the method may also include providing power to the one or more mechanical-to-electrical transducers, the accommodation controller, and the accommodation actuator via a power supply disposed within the eye. The power supply may be charged via a port extending out of the eye (e.g., micro-wire) or may be charged inductively and/or optically. The power supply may be a battery, capacitive structure, or otherwise. In some embodiments, the power supply could be a capacitive structure that is continuously recharged because the intraocular lens is powered inductively from "glasses" worn by the user. The glasses may continuously transmit power to an inductive charging ring, and the power supplied from the glasses is filtered with the capacitive structure.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

The invention claimed is:

1. An intraocular lens (IOL), comprising:
one or more haptic structures having a shape adapted to hold the IOL in an eye, wherein the shape of the one or more haptic structures includes a linear portion connected to an arced portion;
one or more mechanical-to-electrical transducers disposed on the one or more haptic structures to measure a deformation of, a stress in, or a strain in the one or more haptic structures due to mechanical changes in the eye and, in response to the deformation, stress, or strain, output an electrical signal, wherein a first one of the mechanical-to-electrical transducers is disposed on the arced portion of the shape; and
an accommodation actuator electrically coupled to the one or more mechanical-to-electrical transducers, wherein in response to the electrical signal an optical power of the accommodation actuator changes.

2. The IOL of claim 1, further comprising amplification circuitry coupled to the one or more mechanical-to-electrical transducers to receive the electrical signal and amplify the electrical signal.

3. The IOL of claim 2, wherein the amplification circuitry and the one or more mechanical-to-electrical transducers are disposed on the one or more haptic structures.

4. The IOL of claim 2, further comprising an accommodation controller electrically coupled between the one or more mechanical-to-electrical transducers and the accommodation actuator, wherein in response to the electrical signal the accommodation controller determines a magnitude of the change of the optical power.

5. The IOL of claim 4, further comprising:
a power supply electrically coupled to the one or more mechanical-to-electrical transducers, the accommodation controller, and the accommodation actuator, wherein the power supply provides power to the one or more mechanical-to-electrical transducers, the accommodation controller, and the accommodation actuator; and
charging circuitry coupled to the power supply to charge the power supply.

6. The IOL of claim 4, wherein the electrical signal output from the mechanical-to-electrical transducers is commensurate to movement of a pseudophakic capsular bag, occurring during the eye's accommodative process.

7. The IOL of claim 6, wherein predefined movement actions of the pseudophakic capsular bag correspond to predefined optical power settings defined in logic in the accommodation controller.

8. The IOL of claim 1, wherein the one or more mechanical-to-electrical transducers includes at least one of a strain gauge, a pressure sensor, a piezoelectric sensor, piezoresistive sensor, or a capacitive sensor.

9. The IOL of claim 1, wherein a second one of the mechanical-to-electrical transducers is disposed at the linear portion of the shape to sense a second component of the deformation, stress, or strain that is orthogonal to a first component sensed by the first one of the mechanical-to-electrical transducers disposed at the arced portion of the shape.

10. An apparatus including:
an accommodation actuator having variable optical power;
one or more haptic structures having a shape adapted to hold the IOL in an eye, wherein the shape of the one or more haptic structures includes a linear portion connected to an arced portion;
one or more mechanical-to-electrical transducers disposed to measure mechanical changes in the eye when the IOL is implanted in the eye, the one or more mechanical-to-electrical transducers disposed on the one or more haptic structures to measure a deformation of, a stress in, or a strain in the one or more haptic structures, wherein a first one of the mechanical-to-electrical transducers is disposed on the arced portion of the shape; and
an accommodation controller electrically coupled to the accommodation actuator and the one or more mechanical-to-electrical transducers, wherein the accommodation controller includes logic that when executed by the accommodation controller causes the accommodation controller to perform operations including:
receiving an electrical signal from the one or more mechanical-to-electrical transducers in response to the mechanical changes in the eye; and
in response to the electrical signal, changing an optical power of the accommodation actuator proportional to the electrical signal.

11. The apparatus of claim 10, further comprising amplification circuitry coupled between the one or more mechanical-to-electrical transducers and the accommodation controller to amplify the electrical signal output from the one or more mechanical-to-electrical transducers.

12. The apparatus of claim 10, wherein the one or more mechanical-to-electrical transducers includes at least one of a strain gauge, a pressure sensor, a piezoelectric sensor, piezoresistive sensor, or a capacitive sensor.

13. The apparatus of claim 10, wherein the electrical signal output from the one or more mechanical-to-electrical transducers is proportional to movement of a pseudophakic capsular bag, occurring during the eye's accommodative process.

14. The apparatus of claim 10, wherein the haptic structures are disposed on opposite sides of the accommodation actuator, wherein the one or more mechanical-to-electrical transducers are coupled to the haptic structures to sense deformation of the haptic structures.

15. The apparatus of claim 10, wherein the accommodation actuator is at least in part disposed in a transparent encapsulant.

16. A method of active accommodation, comprising:
measuring a mechanical change to a pseudophakic capsular bag in an eye with one or more mechanical-to-electrical transducers disposed on one or more haptic structures having a shape adapted to hold an intraocular lens within the eye, wherein the shape of the one or more haptic structures includes a linear portion connected to an arced portion, wherein the mechanical change is measured by sensing a deformation of, a stress in, or a strain in the one or more haptic structures, wherein a first one of the mechanical-to-electrical transducers is disposed on the arced portion of the shape;
in response to the mechanical change, sending an electrical signal to an accommodation controller electrically coupled to the one or more mechanical-to-electrical transducers; and
adjusting an optical power of an accommodation actuator disposed in the eye, wherein the accommodation actuator is electrically coupled to the accommodation controller.

17. The method of claim 16, wherein the one or more mechanical-to-electrical transducers, the accommodation controller, and the accommodation actuator are included in the intraocular lens.

18. The method of claim 16, further comprising amplifying the electrical signal prior to sending the electrical signal to the accommodation controller.

19. The method of claim 16, wherein predefined movement actions of the pseudophakic capsular bag correspond to predefined optical power settings.

20. The method of claim 16, wherein the mechanical change to the pseudophakic capsular bag is measured via the deformation of the haptic structures.

21. The method of claim 20, further comprising providing power to the one or more mechanical-to-electrical transducers, the accommodation controller, and the accommodation actuator via a power supply disposed within the eye.

* * * * *